United States Patent [19]

Coan

[11] Patent Number: 5,165,409

[45] Date of Patent: * Nov. 24, 1992

[54] TONOMETRY APPARATUS

[76] Inventor: William M. Coan, 39 Southfield Cir., Concord, Mass. 01742

[*] Notice: The portion of the term of this patent subsequent to Aug. 28, 2007 has been disclaimed.

[21] Appl. No.: 508,762

[22] Filed: Apr. 12, 1990

Related U.S. Application Data

[63] Continuation-in-part of Ser. No. 235,347, Aug. 23, 1988.

[51] Int. Cl.$^5$ .............................................. A61B 3/16
[52] U.S. Cl. ................................... 128/652; 128/648
[58] Field of Search .......................... 128/645-652, 128/774; 73/862.36, 862.47, 862.48, 79

[56] References Cited

U.S. PATENT DOCUMENTS

| | | | |
|---|---|---|---|
| 3,308,653 | 3/1967 | Roth | 128/645 |
| 3,934,462 | 1/1976 | Rende | 128/652 |
| 4,729,378 | 3/1988 | Trittenbass | 128/645 |
| 4,766,904 | 8/1988 | Kozin et al. | 128/652 |
| 4,860,755 | 8/1989 | Erath | 128/652 |

FOREIGN PATENT DOCUMENTS

| | | | |
|---|---|---|---|
| 3332724 | 3/1985 | Fed. Rep. of Germany | 128/645 |
| 0457466 | 3/1975 | U.S.S.R. | 128/645 |
| 1168187 | 7/1985 | U.S.S.R. | 128/645 |

*Primary Examiner*—Peter A. Aschenbrenner
*Attorney, Agent, or Firm*—Choate, Hall & Stewart

[57] ABSTRACT

Apparatus for measuring pressure within an eye includes means for increasingly inwardly deforming a surface of the eye by applying a progressively increasing force onto the surface, means responsive to inward deformation of the eye surface for taking a measure related to the amount of the deformation and means for taking a measure related to the amount of the applied force at a sampling time during the progressively increasing force, and electronic means responsive to the deformation-related measuring means and the applied force-related measuring means for determining intraocular pressure from the relation between the measures. Such apparatus includes a housing; a member interposable between a surface of the eye and a portion of the housing, and frontwardly-and-rearwardly moveable with respect thereto; means associated with the housing and the member for providing a force, for example a magnetic repulsion, resisting relative rearward movement of the member so that when the member is interposed between the eye surface and the housing portion and the housing portion is moved toward the eye surface, the member front end deforms the eye surface and the member is moved rearward with respect to the housing against the resisting force; and means such as a Hall effect sensor for determining the position of the member with respect to the housing portion. Also, such apparatus further includes means associated with the member front end for determining the amount of deformation of the eye surface.

25 Claims, 5 Drawing Sheets

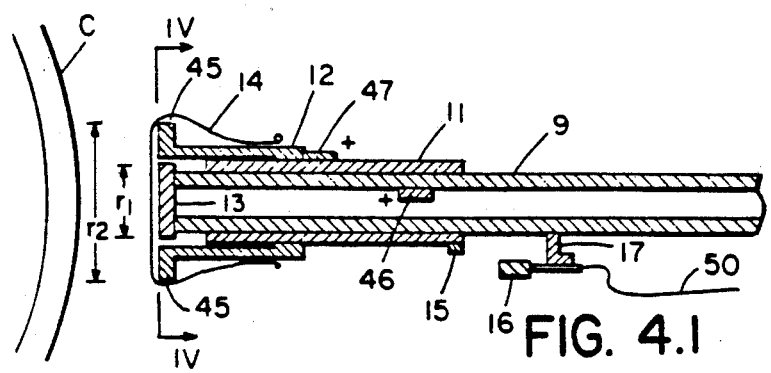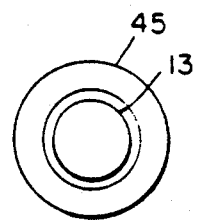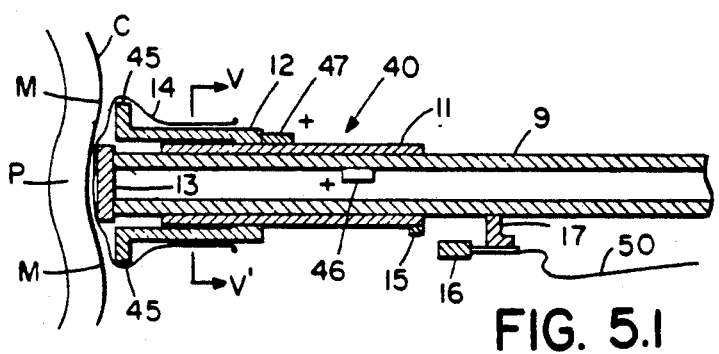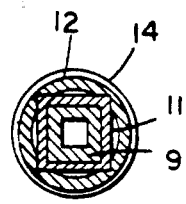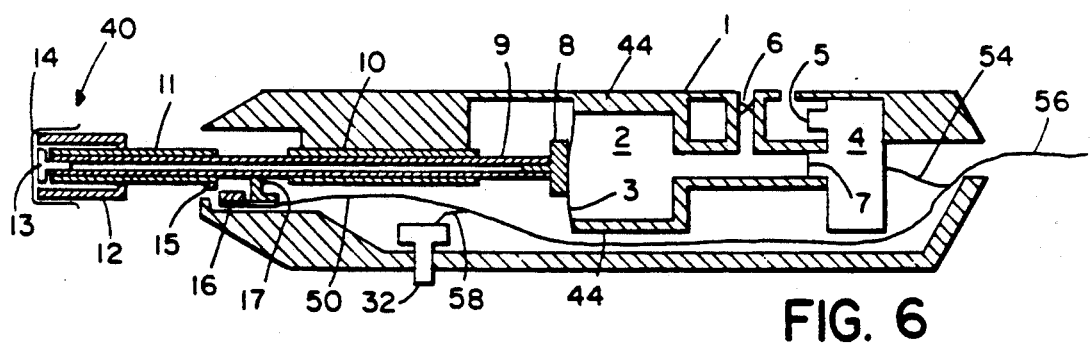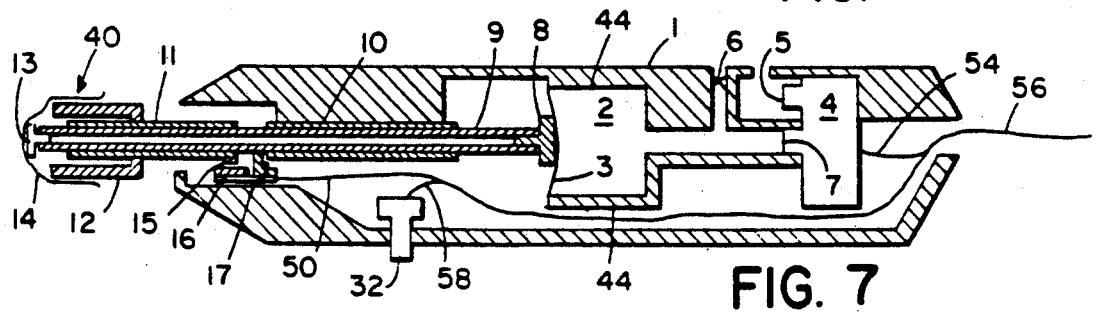

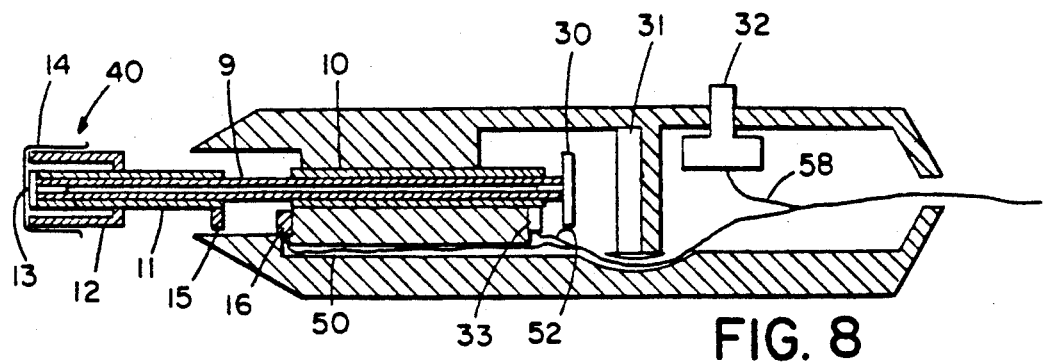
FIG. 8
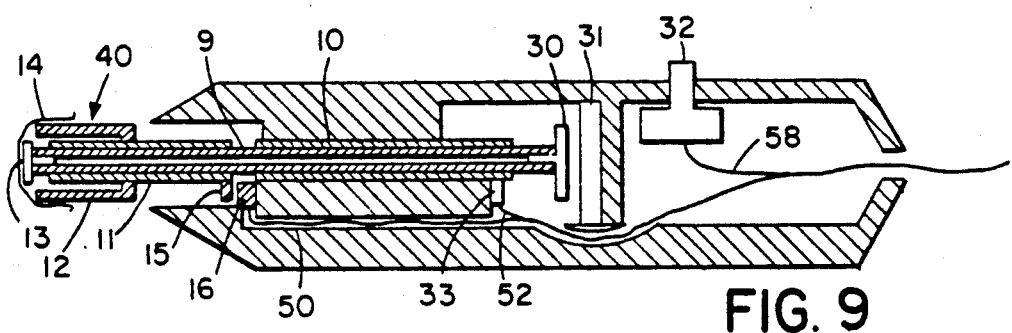
FIG. 9
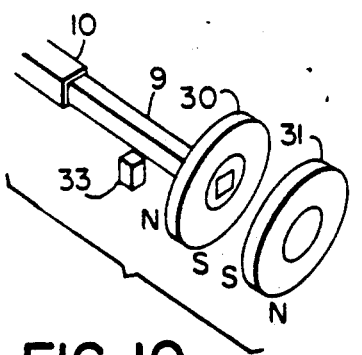
FIG. 10
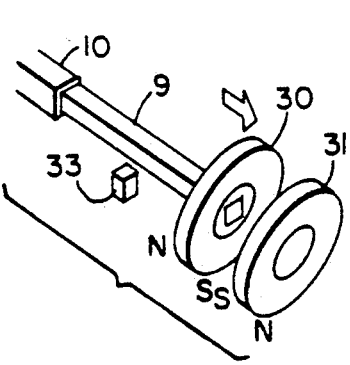
FIG. 10.1
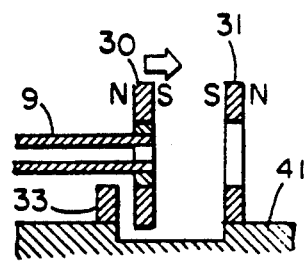
FIG. 11
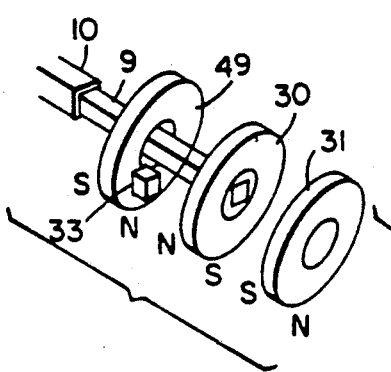
FIG. 12
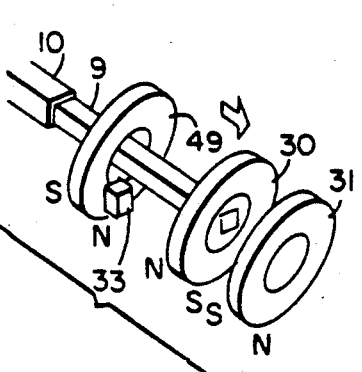
FIG. 12.1
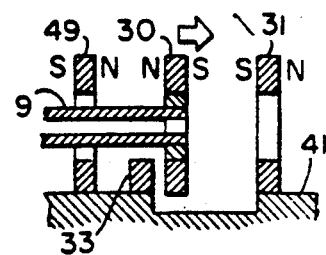
FIG. 13

TONOMETRY APPARATUS

BACKGROUND OF THE INVENTION

This application is a continuation-in-part of copending application U.S. Ser. No. 235,347, filed Aug. 23, 1988, hereby incorporated by reference.

This invention relates to measuring intraocular pressure.

Nearly one percent of the total population of the United States suffers from a form of blindness known as Glaucoma. Glaucoma is characterized by an increase in pressure within the eye, which causes visual defects and ultimately may cause irreversible blindness. As the intraocular pressure rises to abnormal levels, damage is caused to the ocular nerve and surrounding retinal tissues. The patient seldom experiences any symptoms that might indicate that the disease exists until major damage occurs. Typically, the patient's intraocular pressure is elevated, the retinal field is seriously diminished, ocular nerve damage can occur, and there may be some degree of pain.

As part of many standard eye examinations, a test of intraocular pressure (tonometry) is performed to detect the early stages of glaucoma.

A measure of the pressure within the eye is conventionally obtained by depressing to a given depth or flattening to a given extent a portion of a measurement surface of the eye, usually the cornea, and then determining the amount of force required to produce the given flattening or depression. The flattening or depressing is resisted by the resiliency of the measurement surface and by the internal pressure of the eyeball. The determined force is then converted to a measurement of intraocular pressure.

Commonly, the flattening or depression is produced by contacting the tip of an instrument directly onto the measurement surface, and then pressing the tip, whose dimensions are known, against the surface toward the eye. For such measurements to be accurate, the tip of the instrument must be properly oriented with respect to the measurement surface and the direction of pressing toward the eye must be substantially normal to the measurement surface.

Measurement of intraocular pressure using conventional apparatus generally requires that the operator subjectively judge the depth, approach angle, and position of the measuring instrument upon the eye. Operation of such devices depends upon operator skill and consistency. Operator error and the combination of these subjective variables can result in variability in measurements taken by a particular operator from time to time, as well as inconsistency in measurements taken by different operators.

Many tonometers in use employ optical systems that allow the clinician to monitor the amount of flattening or depression of the eye surface to adjust the proper angle and depth of penetration. Such devices typically include a lens that rests directly upon the eye, through which the operator views the tear meniscus to judge the correctness of the flattening or depression at the time of measurement. Such devices typically require equipment for holding the patient's head in a particular position for a time, and often employ slit lamp equipment to aid in alignment. Some time is required to set up such apparatus preparatory to each measurement.

It is generally accepted that, when properly and skillfully used, direct contact tonometers can give more valid indications of intraocular pressure, and can provide more reliable diagnosis of early stages of glaucoma, than can other types of tonometers.

The anterior chamber within the eyeball behind the cornea and in front of the lens is filled with a fluid termed the aqueous humor. In the healthy eye, the aqueous humor circulates out from the anterior chamber, and glaucoma can be caused by a partial or full obstruction restricting this flow. A consequent rise in intraocular pressure can occur long after the restriction of flow has begun, so that the disease process may have been under way for some time before any elevated intraocular pressure can be detected.

In the healthy eye the aqueous humor can be caused to flow out from the anterior chamber more rapidly by pressing inward onto the cornea for a time, in effect massaging the aqueous humor out from the anterior chamber, resulting in a measurable reduction of pressure within the eye. In a technique known as tonography, the capacity for flow of the aqueous humor from the anterior chamber is determined by imposing pressure onto the cornea, typically by resting a weight upon the corneal surface while the patient is in a supine posture and then taking a time series of intraocular pressure measurements. Tonography is being used with increasing frequency, as tonography has been found to yield greater diagnostic and prognostic value that conventional tonometry alone for some pathologies.

A variety of disease pathogens can be found on the surface of the eye, and particularly in the fluid film that covers the eye. These include, for example, pathogens causing herpes and, possibly, acquired immune deficiency syndrome (AIDS). A disadvantage of conventional direct contact tonometers is that because they must touch the eye, they can transmit such diseases from eye to eye and from patient to patient.

It has been suggested that direct contact tonometers be provided with disposable prophylactic covers, for preventing transmission of disease pathogens from one eye to another. Damage to the eye sometimes occurs, owing to individual tissue susceptibility to injury, to mishap, or to operator error. Many known tonometers, including those which the operator aligns by employing a lens in contact with the measurement surface, cannot be modified to accommodate such covers. Those devices that have been so modified are, at least partly as a result, not sufficiently sensitive to provide accurate measurements, and they have not been accepted by the medical community as clinically practical measurement devices.

Apart from error due to subjective judgments and error of the operator, measurement error often is an effect of the design of the particular device, and especially of the particular transduction scheme.

In early tonometers, lever systems were actuated by metallic springs or cams to provide a mechanical analog of the intraocular pressure. The precision of such devices depends upon the characteristics of compressibility of the spring systems and individual units produce differing measurements to the extent that their spring systems differ. Spring fatigue and changes in temperature can cause changes in measurement.

In other known devices strain gauges are directly coupled to the measurement surface through a metal shaft that directly contacts the eye. These, too, are affected by variations in temperature, and they can be plagued with signal conditioning problems and poor schemes for calibrating the strain gauge bridges. Some such systems cannot be calibrated by the user and consistency in manufacture or materials cannot be assured in the commercial production of such instruments.

In other known tonometers a piezoelectric crystal transducer is directly coupled to a metallic plunger which directly contacts the eye. Piezoelectric crystals can be affected by small and practically undetectable changes in temperature. Because piezoelectric transducers respond not only to force but also to temperature, varying temperatures in ambient air as well as body heat transferred through the shaft from the patient to the piezoelectric crystal can interfere with precise measurement of the intraocular pressure. Moreover, the piezoelectric crystal transducer can be affected not only by temperature but also by the velocity with which the force applied to the measurement surface changes. Such devices can yield a voltage analog signal that combines contributions of the applied force, the velocity at which the force is increased, and the temperature of the test environment. Further, such devices typically require use of a microprocessor for calibration and for adjustment for the non-linearity of the transducer mechanism. The user cannot easily recalibrate the device in the field.

In devices known as "non-contact" or "airpuff" tonometers, compressed gases are directed at the cornea to flatten or depress it. These are referred to as "non-contact" devices because apart from one or more bursts of air fired or released toward the eye from a predetermined distance they do not come into contact with the measurement surface. Typically in such devices an incident light wave is transmitted by light emitting diodes to the cornea, which reflects it back to phototransducers within the device. As the measured pressure of the compressed gas jet is directed toward the measurement area, the surface is flattened and a measure of reflected light yields a relative measurement of intraocular pressure. Such devices are generally considered cumbersome to operate, and obtaining consistent measurements depends upon the skill and technique of the operator in aligning the instrument at the proper distance and orientation to the eye. They are generally regarded by health care workers as useful initial screening devices, but they are not generally accepted as providing accurate measurements. The major attribute of their acceptance has been the isolation of the patient from the device to inhibit disease transmission. The patient often complains of the pain associated with the blast of air that must be delivered to the eye to obtain a measurement, and many patients are often reluctant to be measured a second time by such devices.

SUMMARY OF THE INVENTION

Tonometry apparatus according to the invention employs means for applying force upon a surface of the eyeball to deform, that is, to flatten or depress, the eyeball surface, and means for measuring the amount of deformation and for measuring the amount of force applied to the eyeball surface, as described generally in my copending application U.S. Ser. No. 235,347. The intraocular pressure is determined by determining the amount of deformation produced by applying a given force or, alternatively, by determining the force required to depress or flatten the surface by a given amount.

In general, in one aspect, the invention features apparatus for measuring pressure within an eye, including an air chamber supported by a housing, the air chamber having a deformable wall portion, a pressure sensor for measuring air pressure within the chamber, and a member interposable between a surface of the eye and the deformable wall portion. The member has a rear end and a front end, is substantially non-compressible along its front-to-rear direction, and is engaged with the housing such that it is frontwardly-and-rearwardly moveable with respect to the deformable chamber wall portion. When the member is interposed between the eye surface and the deformable chamber wall portion, and the housing is moved in a direction that shortens the distance between the eye and the air chamber, the front end of the member inwardly deforms the eye surface and the rear end of the member inwardly deforms the deformable wall portion, raising the pressure within the air chamber, as measured by the pressure sensor.

In preferred embodiments the air chamber is a bladder, preferably made of latex rubber; the deformable portion of the air chamber wall is a diaphragm, preferably an elastic diaphragm, most preferably made of an elastomer such as latex rubber; the member includes a shaft coupled in slidable relation to the housing; the pressure sensor includes a pressure transducer; the apparatus further includes means responsive to the pressure sensor for displaying a measure of the pressure; the apparatus further includes means responsive to the pressure sensor for recording the measure; the apparatus further includes a valve which when open provides communication between the air chamber and atmospheric air; the apparatus further includes means for aligning the member with the eye surface during the measuring; the apparatus further includes a prophylactic membrane interposed between the front end of the member and the eye surface.

In embodiments using a measure of the pressure in an air chamber as a measure of the force used for flattening or inwardly deforming the eye surface, the apparatus preferably employs a gas pressure coupling which exerts equal pressure upon all legs of the transducer equally. The device is not affected substantially by changes in ambient temperature, or by the body temperature of the patient. Pressure equalization permits measurements to be made independently of atmospheric pressure.

In general, in another aspect, the invention features apparatus for measuring pressure within an eye, including a member, substantially non-compressible along its front-to-rear direction and engaged with a housing such that it is frontwardly-and-rearwardly moveable with respect to the housing, means for resisting rearward movement of the member with respect to the housing, and means for detecting the frontward-to-rearward position of the member with respect to the housing. When the front end of the member is interposed between the eye surface and the housing is moved toward the eye, the front end of the member increasingly inwardly deforms the eye surface while the rearward movement of the member with respect to the housing is increasingly resisted, and the position of the member with respect to the housing at the point where the eye has been deformed to a specified degree provides a measure of the pressure within the eye.

I have now discovered that substantial improvements in performance of the apparatus and in convenience of use can be obtained by moveably affixing near the front end of the member a collar that is frontwardly-to-rearwardly moveable with respect to the front end of the member in response to deformation of the eye surface, and using a Hall effect sensor and associated magnet in the probe tip for measuring the front-to-rear position of the collar to provide a determination of the amount of depression or flattening of the eyeball surface; or by employing means for increasingly resisting the rearward movement of the member as the member is forced rearward with respect to the housing, and using a Hall effect sensor to determine the front-to-rear position of the member in the housing as a measure of the rearward force on the member; or by using Hall effect sensors in performing both measurements.

In preferred embodiments, the means for resisting rearward movement of the member comprises a deformable wall portion of a closeable air chamber; the apparatus further includes means for resisting frontward movement of the member with respect to the housing; the means for resisting frontward or rearward movement of the member with respect to the housing includes magnetic field-producing means associated with the member and with the housing; the magnetic field-producing means associated with the member includes a magnet affixed to the member, preferably to the rear end of the member, and the magnetic field-producing means associated with the housing includes a magnet affixed to the housing; the magnets are arranged so that rearward movement of the member with respect to the housing brings like poles of a member-associated magnet and of a first housing-associated magnet closer together; and so that frontward movement of the member with respect to the housing brings like poles of a member-associated magnet and of a second housing-associated magnet closer together; the polarities of the magnetic fields are oriented along the direction of frontward-and-rearward movement of the member; the magnets are axially aligned with respect to the frontward-and-rearward movement of the member; the position detecting means includes a Hall effect sensor, preferably affixed to the housing and responsive to position of a magnetic field associated with the member or affixed to the member and responsive to position of a magnetic field associated with the housing; and the member includes a rod having a rectangular, preferably square, section.

In general, in another aspect, the invention features apparatus for measuring the pressure within an eye, including a member having a front end arranged and adapted to deform the eye surface when the member is pressed inward upon the eye surface, a force sensor arranged and adapted to measure the force required for the front end to deform the eye surface to a specified degree, and a deformation sensor for determining when the eye surface has been deformed to the specified degree.

In preferred embodiments the deformation sensor includes a collar, frontwardly-and-rearwardly moveable with respect to the front end of the member in response to inward deformation of the eye surface by the front end of the member, and a position sensor for determining the frontward-to-rearward position of the collar with respect to the member; preferably, the position sensor includes a Hall effect sensor affixed to the member and arranged to be responsive to the position of a magnetic field associated with the collar, more preferably to a magnetic field produced by a magnet affixed to the collar.

In other preferred embodiments the deformation sensor includes an alignment sensor including a plurality of contacts affixed to the member and an element adapted and arranged to form electrical contact with one of the contacts when the member is aligned with the eye surface and the eye surface has been deformed to the specified degree. Preferably on these embodiments the contact forming element is adapted and arranged to form electrical contact with two of the contacts when the member is aligned with the eye surface and the eye surface has been deformed to the specified degree; the sensor includes at least three such contacts and the element is adapted and arranged to form electrical contact with three of the contacts when the member is aligned with the eye surface and the eye surface has been deformed to the specified degree; the element includes an element moveably affixed to the member, the element resiliently moveable forwardly and rearwardly in relation to the member; the element includes an annular piece; the contacts are sector shaped and each of the contacts has a contact surface arranged in a plane perpendicular to a frontward-rearward axis of the member; the apparatus further includes means for resiliently urging the element frontwardly; the urging means includes a spring; the spring includes a helical compression spring; the urging means includes an elastic membrane.

The tonometer of the invention can be used in any of its embodiments to accurately measure intraocular pressure through a disposable prophylactic sheath, or prophylactic membrane.

The prophylactic sheath can be disposed of after each measurement and replaced before the next measurement, thus helping to prevent transmission from eye to eye and from patient to patient of pathogens that may be present on the surface of the eye. Moreover, the prophylactic sheath helps to ensure that the soft tissues of the cornea or the sclera, which are contacted during measurement, are not scratched or otherwise damaged by the instrument. Use of the prophylactic sheath does not interfere with operation of the device or with precision or accuracy of measurement.

The sheath is smooth and non-irritating, and it helps to protect the eye from direct injury that might result from operator error or inadvertent movement of the eye during contact.

The precision of measurement is not affected by temperature deviations or by changes in atmospheric pressure.

The apparatus can be used by persons having no special training or experience, and provides accurate reproducible measurements objectively without respect to the level of skill of the operator.

In some embodiments the apparatus coordinates an alignment sensing system with a pressure measurement system so that a pressure measurement is held and displayed automatically at the moment that specified alignment and deformation criteria are met. The apparatus then notifies the operator that the alignment criteria have been met and that a measurement has been held and displayed.

In embodiments employing a deformation sensor in the form of a collar, and using a Hall effect sensor to determine the rearward displacement of the collar with respect to the tip, the tip assembly can be sufficiently miniaturized that misalignment is unlikely to occur to an extent that would result in inaccurate measurement, even in the hand of a relatively inexperienced user; and a misalignment that exceeds a predetermined tolerance can be automatically detected by the tip assembly, providing a warning to the operator or preventing a record of a measurement.

In embodiments employing magnetic fields for resisting the frontward movement of the member as well as its rearward movement, the frontward-to-rearward position of the member is, in the absence of a rearward force, effectively fixed by the competitive effects of the two fields, irrespective of the orientation of the apparatus.

The tonometer of the invention can be employed with the patient in either a supine or sitting position. Thus the invention provides for measurement of intraocular pressure during ophthalmologic surgery, with the patient in any of a variety of positions, or for ocular examination of patients who cannot be elevated, as well as during customary routine examinations, with the patients seated.

The device can be battery powered for improved portability and convenience in use, and to avoid danger of electric shock to the patient. It can be used with extremely low power digital and analog technology to preserve battery power.

The apparatus can conveniently be used in tonography, by adding a weight to the member, and allowing the front end of the member, carrying the weight, to rest for a time upon the cornea of the supine patient, and performing a time series of intraocular pressure measurements with the patient in a supine posture.

DESCRIPTION OF PREFERRED EMBODIMENTS

Preferred embodiments of the invention will now be described, beginning with a brief description of the drawings.

Figure 1:
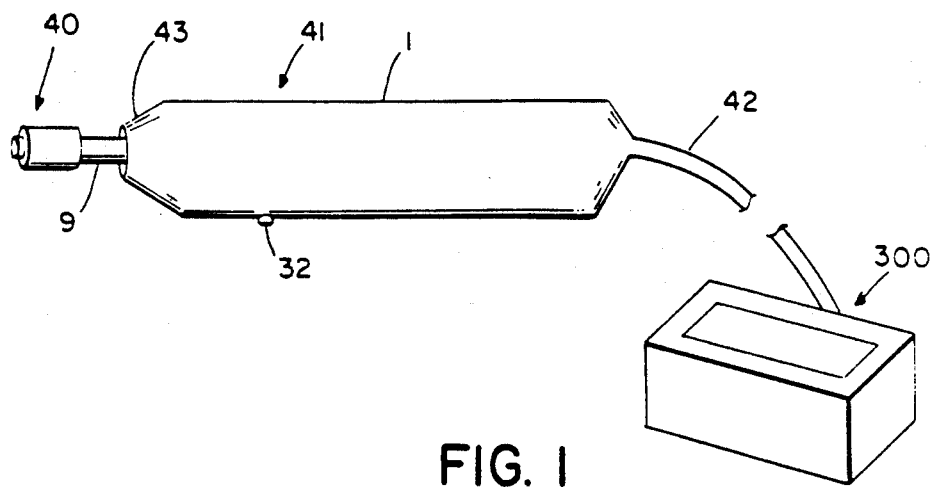
FIG. 1 is a perspective view of Tonometer apparatus of the invention.

FIG. 4.1 is a somewhat diagrammatic view of a part of the apparatus of FIG. 1, made in section thru the axis of the probe tip assembly, showing the probe tip assembly ready for taking a measurement.

FIG. 4.2 is a somewhat diagrammatic sectional view, taken at IV—IV in FIG. 4.1, thru the apparatus of FIG. 1.

FIG. 5.1 is a somewhat diagrammatic sectional view, as in FIG. 4.1, of the apparatus of FIG. 1, showing the probe tip assembly in use in contact with the eyeball surface during measurement.

FIG. 5.2 is a somewhat diagrammatic sectional view, taken at V—V in FIG. 5.1, thru the apparatus of FIG. 1.

Figure 2:
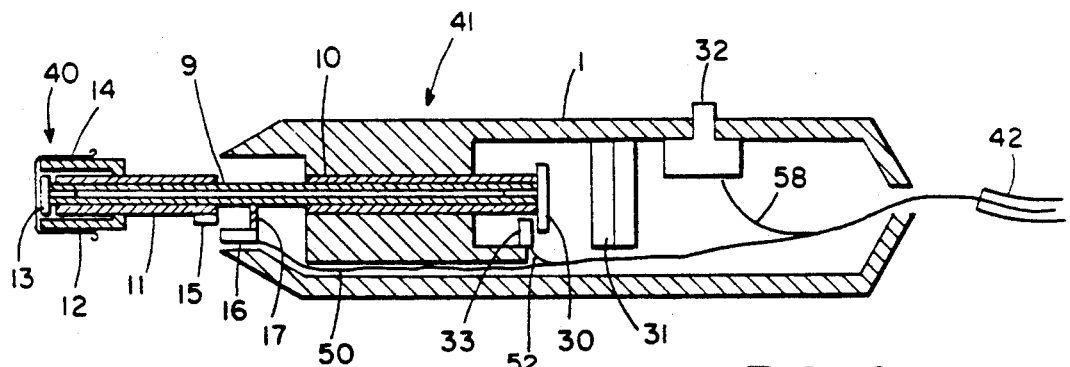
FIG. 2 is a somewhat diagrammatic view of the apparatus of FIG. 1, partly in section thru the axis of the force-measuring assembly, showing the apparatus ready for taking a measurement.

FIG. 6 is a somewhat diagrammatic sectional view, taken as in FIG. 2, of alternative force-measuring assembly according to the invention, showing the apparatus ready for taking a measurement.

FIG. 7 is a somewhat diagrammatic sectional view of apparatus as in FIG. 6, showing the apparatus in use during a measurement.

FIG. 8 is a somewhat diagrammatic sectional view, taken as in FIG. 2, of alternative apparatus according to the invention, showing the apparatus ready for taking a measurement.

FIG. 9 is a somewhat diagrammatic sectional view of the apparatus as in FIG. 8, showing the apparatus in use during a measurement.

FIGS. 10 and 10.1 are diagrammatic views in perspective of a portion of the force-measuring assembly of the apparatus in an embodiment employing opposing magnetic fields to resist rearward movement of the member, as for example in FIG. 2 or FIG. 8, illustrating arrangement and relative movement of magnets on the moveable member and on the housing.

FIG. 11 is a sectional view thru the front-to-rear axis of the apparatus of FIG. 10.

FIGS. 12 and 12.1 are diagrammatic views in perspective, as in FIGS. 10, 10.1, of alternative force-measuring assembly employing an additional annular magnet, illustrating arrangement and relative movement of magnets on the moveable member and on the housing.

FIG. 13 is a sectional view thru the front-to-rear axis of the apparatus of FIG. 12.

Figure 14:
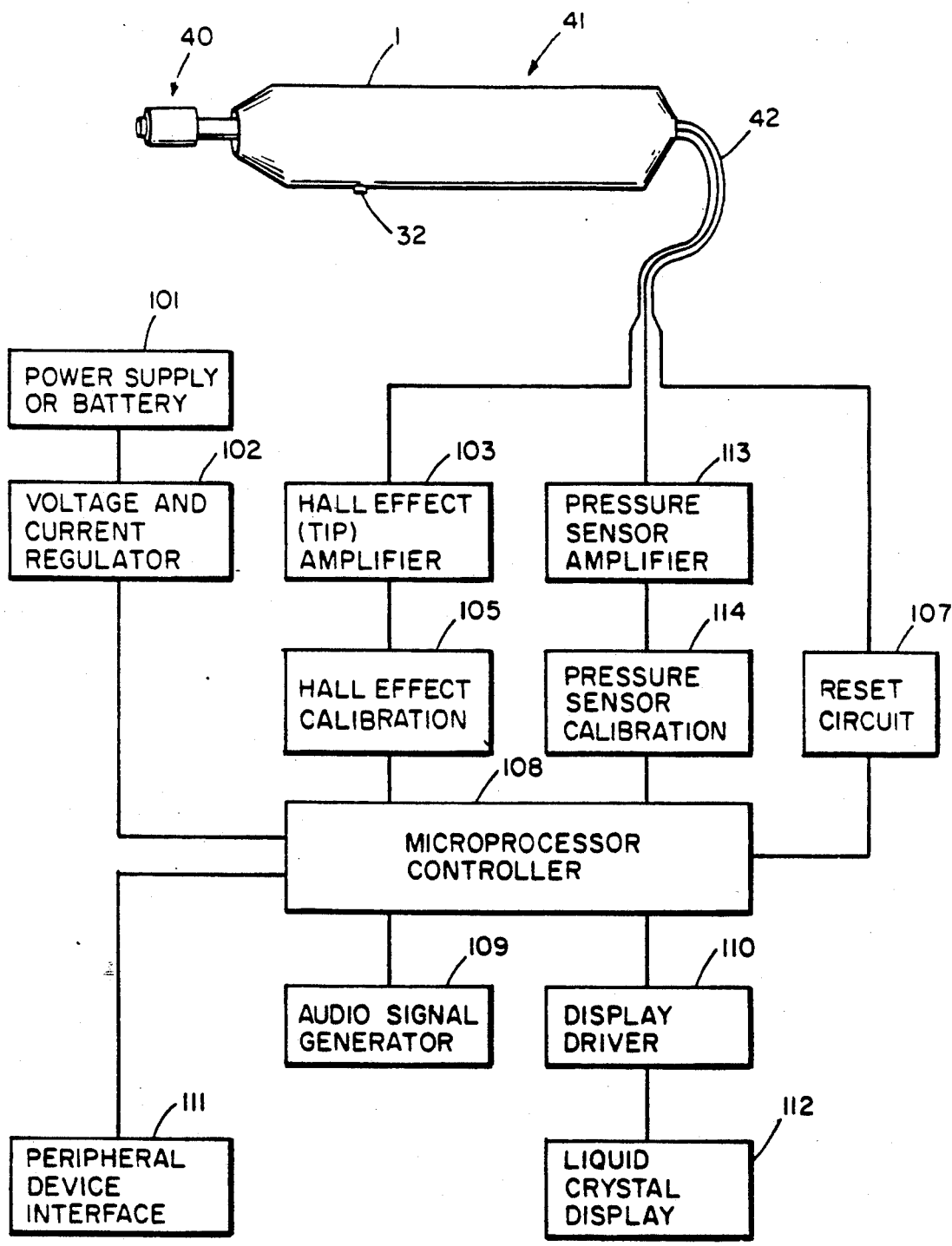
Figure 15:
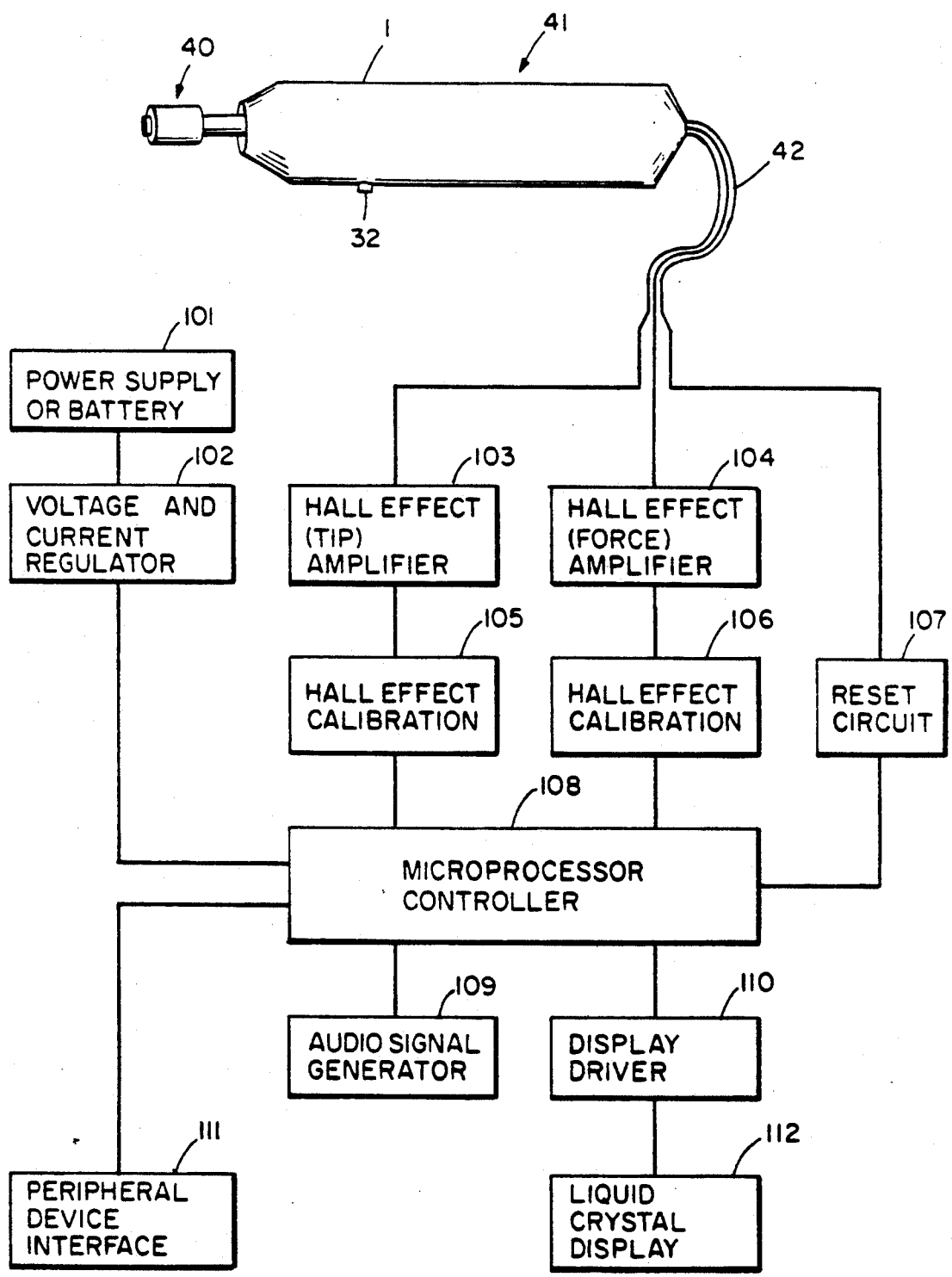

FIGS. 14 and 15 are block diagrams, respectively, of alternative electrical circuitry of the apparatus according to the invention.

STRUCTURE AND OPERATION

The invention provides tonometry apparatus in various embodiments capable of providing accurate and reproducible measurements of intraocular pressure, while permitting the use of a disposable sheath for covering the part of the apparatus that touches the eye during measurement. In various embodiments, the invention features probe tip apparatus which provides for sensitive indication of proper depression or flattening of the eye surface; and features apparatus which provides for accurate measurement of the force necessary to produce the depression, unaffected by atmospheric conditions in the testing milieu or by whether the patient is in an upright or a supine posture, as a measure of the intraocular pressure.

Preferred tonometer apparatus of the invention is shown by way of example in a perspective view in FIG. 1. Referring now to FIG. 1, a housing, shown generally at 41, includes handle portion 1, from which nose portion 43 generally projects. A probe tip assembly, shown generally at 40, is affixed to a shaft member 9, which is slidably engaged within housing 41 such that the shaft member and the probe tip attached to the shaft member can slide frontwardly and rearwardly with respect to the housing, as described more fully below. A display, shown generally at 300, is connected to housing 1 via cable 42. Cable 42 contains wires (not shown in FIG. 1) which provide for electrical connections between parts of display 300 and parts of housing 41, as further described below with reference to drawings in sectinal view. Reset switch 32 is provided in housing 1 for resetting the electrical circuits of the apparatus between readings, as described below.

Figure 3:
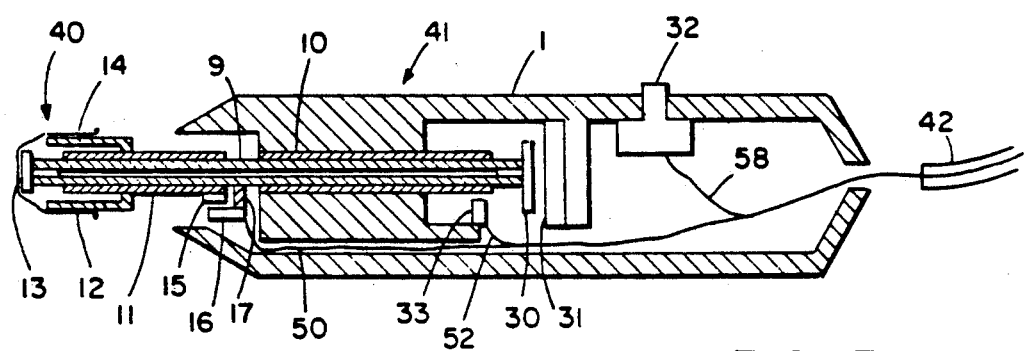
FIG. 3 is a view of the apparatus as in FIG. 2, showing in sectional view the force-measuring assembly in use during a measurement.

Referring now to FIGS. 2 and 3, shaft member 9 preferably is a rigid tube having a rectangular (preferably square) section, and bushing 10 in housing 41 provides a low-friction bearing surface for frontward and rearward sliding movement of the shaft member. Probe tip assembly 40, as described more fully below with reference to FIGS. 4.1 and 5.1, includes a generally disc-shaped probe tip 13, affixed at the front end of shaft member 9, and a generally cylindrical or collar-shaped probe tip housing 12, affixed to a bushing 11 which is slidably engaged with shaft member 9 to provide low-friction frontward and rearward movement of the probe tip housing upon the front portion of shaft member 9. The probe tip housing and the probe tip are covered by a removable and disposable prophylactic latex cover 14 prior to use.

FORCE

With reference now particularly to FIGS. 2, 3, 10, 10.1 and 11, toroidal magnets 30, 31 are affixed respectively to the rear end of shaft member 9 and to housing 1. Magnets 30, 31 are axially aligned so that their polarities are antiparallel. For instance, the North magnetic pole of the shaft magnet 30 might face rearward toward the North magnetic field of the stationary magnet 31 or, as illustrated for example in FIGS. 10, 10.1 and 11, the South magnetic poles of the two magnets 31 and 30 could similarly be arranged to face each other to yield the same effect.

As a result of this arrangement, the opposing magnetic fields generated by magnets 30, 31 mutually repel when the magnets are approximated, producing a force resisting rearward movement of the shaft member 9 with respect to the housing 1. This resisting force increases as the shaft member is moved further rearward, so that when the shaft is at rest the amount of rearward force on the shaft can be determined by the front-to-rear position of the shaft relative to the housing. The front-to-rear position of the shaft is determined by shaft position sensor 33, which is mounted on housing 41. Shaft position sensor 33 is a "Hall effect sensor", preferably of the linear HE type, such as is available, for example, as Sprague UGN-3503U (Concord, N.H.), and is arranged so that it is responsive to the magnetic field produced by magnet 30. Thus, shaft position sensor 33 determines the proximity of the shaft magnet 30 by producing an electrical current (or, alternatively, raising an electrical potential) that is related to the strength of the magnetic field produced by shaft magnet 30 and the proximity of the shaft magnet 30 to shaft position sensor 33.

The magnetic sensor 33 can be arranged as illustrated for example in FIGS. 2, 3, 10, 10.1 and 11 such that when the shaft member 9 is moved rearward, moving the magnet 30 away from the sensor 33 in a rearward motion, the electrical current (or potential) from the sensor is reduced in proportion to the strength of the magnetic field at the sensor 33 as the magnet 30 travels away from the sensor. In other words, in this arrangement, when the magnet 30 is close to the sensor 33, the sensor produces a maximum amount of current (or raises a maximum potential). When the magnet 30 is driven rearward away from the magnetic sensor 33, the magnetic field sensed by the sensor 33 is reduced and, consequently, the sensor produces less electrical current (or raises a lower potential). As strength of the magnetic field produced by the magnet 30 does not change, and as the sensor 33 is responsive to the strength of the magnetic field at the sensor, the sensor 33 detects different magnetic field strenghts as the magnet is moved nearer or farther from the sensor. Thus, the magnetic sensor provides an accurate indication of the position of the magnet 30 relative to the stationary magnetic sensor 33, which is calibrated to a measure of the force applied to the eye by the tip.

When a rearward force is applied to the shaft member, causing the probe tip 13 to move rearward with respect to the housing 41 and the magnet 31, shaft 9 brings the rear surface of magnet 30 toward magnet 31 and away from magnetic sensor 33, as shown for example in FIGS. 3, 10, 10.1 and 11. As the distance is increased between magnet 30 and magnetic sensor 33, the magnetic sensor produces an electrical current (or raises an electrical potential) whose magnitude is related to the position of the magnetic field of magnet 30. In this arrangement, the sensor current (or potential) falls as the distance increases between the magnet and the sensor, providing an electrical analog of the distance between the magnet and the sensor, and thus of the front-to-rear position of the shaft 9 in relation to the housing 1. Because the rearward movement of the magnet 30 is opposed by magnet 31, an increase in force upon probe tip 13 is necessary to increase the relative distance between sensor 33 and shaft magnet 30. The opposing force of the magnets can be calibrated in relation to the distance of the shaft magnet 30 from the sensor 33, and in this way the front-to-rear position of the shaft magnet in relation to the sensor may be converted into an analog of the force or pressure applied to the shaft foot plate 13. By plotting the force required to displace the shaft 9 rearward from point of rest toward the stationary magnet 31 (to a point where the greatest opposing magnetic force is encountered) as a function of the distance traveled by the magnet 30 from the sensor 31, an accurate analogue of force from distance or proximity can be obtained.

With reference now to FIGS. 12, 12.1 and 13, the front-to-back position that the shaft assumes when no rearward pressure is imposed on the tip can be fixed by mounting a third annular magnet 49 on the housing 41 in a position frontward from the shaft magnet 33. The polarity of magnet 49 is axially aligned with, and antiparallel to, the polarity of shaft magnet 33, and shaft 9 passes through the hole in toroidal magnet 49, as indicated for example by the letters N and S next to the magnets in FIGS. 12, 12.1 and 13. The start position for the shaft between measurements is held by the mutually repelling magnetic fields of magnets 33, 49, and 31, effectively irrespective of the orientation of the device.

Alternatively, the rearward movement of the shaft member 9 can be resisted by resilient mechanical means, such as, for example, by a spring or by an elastic membrane against which the rear end of the shaft member 9 presses.

In such embodiments, the rearward position of the member can be detected by magnetic field sensing means, generally as described above, for example by mounting a small magnet on the shaft member and placing a Hall effect sensor on the housing so that as the shaft member 9 moves frontward or rearward, the distance between the small magnet and the sensor changes. Or, alternately, in an embodiment using an elastic membrane to resist rearward movement of the shaft member, the membrane can form a deformable wall portion of a closeable chamber, and a measure of the pressure within the chamber can form a analog of the front-to-rear position of the member (and thus of the rearward force on the member, imposed by the resistance of the eye surface to deformation), as described generally in my copending application U.S. Ser. No. 235,347.

With reference now to FIGS. 6 and 7, showing such an alternative embodiment of the force-measuring means, disc-shaped plunger 8 is affixed to the rear end of shaft member 9. Housing handle portion 1 contains air chamber 2, enclosed by chamber wall 44, a portion of which is constructed of an elastic membrane material, such as a latex rubber sheet, forming a deformable wall portion 3. When shaft member 9 is moved rearward with respect to housing 41, sliding in low-friction bushing 19, shaft member 9 brings the rear surface of plunger 8 in contact with the front surface of deformable front portion 3 of wall 44. Continued rearward movement of shaft member 9 causes plunger 8 to rearwardly displace deformable front wall portion 3, as shown in FIG. 7.

Handle 1 contains a pressure transducer, shown schematically generally at 4, which communicates with air chamber 2 by way of air chamber port 7. Pressure transducer 4 is provided with differential intake port 5, which communicates with ambient air, and air chamber 2 communicates with pressure equalizer valve 6, by which air can be taken into or exhausted from chamber 2. When pressure equalizer valve 6 is closed, as will be appreciated by one skilled in the art of pressure measurement, pressure transducer 4 in effect compares the pressure within air chamber 2 via air chamber port 7 with ambient atmospheric pressure via differential intake port 5. When pressure equalizer valve 6 is open to the atmosphere, the two pressures are equal. Rearward displacement of deformable wall portion 3 decreases the volume of air chamber 2; when air chamber valve 6 is open, such a volume decrease results in exhausting a portion of the air out from air chamber 2 through air chamber valve 6. On the other hand, when pressure equalizer valve 6 is closed, rearward displacement of deformable wall portion 3 compresses the air contained within air chamber 2 and increases the pressure sensed by the pressure transducer via air chamber port 7. Because the difference between the pressure within closed air chamber 2 and ambient air is related to the extent of deformation of deformable wall portion 3, which in turn is related to the extent of movement of the shaft member 9 against the resistance of the deformable wall portion 3, the pressure sensed by pressure transducer 4 provides an analog of the position of the shaft member in relation to the housing. As described above, this provides an analog of the pressure within the eye whose surface is being deformed by pressing the probe tip inward against the eye surface.

Housing 41 is preferably molded of a sturdy plastic. Wall 44 of air chamber 2 can be rigid except for the deformable portion, which can be made of any resiliently deformable material, but which is conveniently made from latex rubber sheet; or, alternatively, air chamber 2 can be formed entirely as a bladder made of latex.

Pressure transducer 4 is preferably of the gage pressure type, such as, for example, one of the SCX Series transducers, available commercially from SenSym, 1255 Reamwood Avenue, Sunnyvale, Calif. 94089.

DEFORMATION AND ALIGNMENT

A measure of the depression or flattening of the surface of the eyeball by the probe tip is made by means of the probe tip assembly 40. With particular reference now to FIGS. 4.1, 4.2 and 5.1, 5.2, a probe tip button 13 is affixed to the front end of shaft member 9. Collar-shaped probe tip housing 12, affixed to bushing 11, is slidably movable frontwardly and rearwardly upon the front portion of shaft member 9. The front end of probe tip housing 12 is provided with an annular flange 45. Probe tip button 13 and flange 45 are covered by a removable and disposable prophylactic latex cover 14. As is described more fully below, when the probe tip assembly, covered by the prophylactic sheath, is brought into contact with the eye surface, the front surface of the probe tip button 13 is at first approximately in the same plane as the front surface of the flange 45. Then as the operator moves the apparatus toward the eye to press the probe tip with increasing force against the eye surface, so that the probe tip button inwardly deforms the eye surface, an annular region M of the eye surface about the margin of the probe tip button presses rearward against the front surface of the annular flange, causing the collar-shaped probe tip housing to move rearward on the shaft member. As the deformation increases, the probe tip housing is moved further rearward and, as a result, the front-to-rear position of the tip assembly 40 in relation to the shaft 9 can provide an analog of the amount of deformation of the eye surface.

Following a measurement, tip assembly 40 can be returned to a more frontward position (preferably bringing the front surface of flange 45 into a coplanar relation with the front surface of tip button 13) by use of urging means such as, for example, magnetic repulsion having a magnitude great enough to overcome frictional resistance between the bushing 11 and the shaft member 9, but not great enough to contribute to error in the measurement, that is, to interfere substantially with the rearward force on the annular flange 45 by the deforming eye surface during measurement. With reference to FIGS. 4.1 and 5.1, such an urging force can be provided as follows. A small magnet 46 is secured to the lumenal surface of the wall of hollow shaft member 9, and another small magnet 47 is secured to the tip assembly. Magnets 46, 47 have their magnetic poles oriented antiparallel and front-to-back with respect to the movement of the bushing 11 on the shaft 9, as suggested by the + signs near the magnets in the Figs. The repulsion by the opposing magnetic fields urges the tip assembly 40 frontwardly with respect to the shaft member, irrespective of the orientation of the device, and making the apparatus useful with the patient facing upward or horizontally, or any direction. This frontward urging force additionally aids in reducing front-to-back displacement of the tip assembly that a latex sheath might cause.

The front-to-rear position of the probe tip assembly 40 in relation to the shaft member 9, and thus to the probe tip button 13, preferably is measured by magnetic field sensing means, much as described above with reference for example to FIGS. 2 and 3 for measuring the front-to-rear position of the shaft member in relation to the housing by magnetic field sensing means.

One arrangement of magnetic field sensing means for determining the relative front-to-rear position of the probe tip assembly is shown by way of example in FIGS. 4.1 and 5.1. Tip magnet 15 is affixed to bushing 11 in such a position that tip magnet 15 will come into closer proximity to tip position sensor 16 when tip assembly 40 is forced rearward by applying force upon the most forward portion of tip assembly 40, that is, upon at least a portion of the front surface of flange 45.

Magnet 15 is affixed to tip bushing 11, and tip position sensor 16 is affixed by way of bracket 17 to shaft member 9. Tip position sensor 16 is a Hall effect sensor, and is arranged so that it is responsive to the magnetic field generated by the tip magnet 15 as the tip assembly 40 slides frontwardly and rearwardly upon shaft member 9, as shown particularly in FIGS. 4.1 and 5.1. That is, as the tip assembly 40 moves with respect to the shaft, the distance between tip magnet 15 and tip position sensor 16 changes, resulting in a change in an electric signal produced by the position sensor 16. The position of the tip assembly 40 with respect to the probe tip 13 is thus accurately indicated by the signal produced by the tip position Hall effect sensor.

FIG. 4.1 is a somewhat diagrammatic sectional view of the probe tip assembly ready for taking a measurement, and prior to placement upon the eye. The magnet 15 produces a magnetic field which is detected by the magnetic sensor 16. Because the distance between magnet 15 and magnetic sensor 16 is at this point maximal, the magnetic field detected by the magnetic sensor is minimal and the sensor produces a very small electric current (or raises a relatively small potential). FIG. 5.1 shows a rearward displacement of the tip assembly 40 as the shaft 9 is forced against the surface of the eye. As the operator, holding the apparatus by the handle portion of the housing, moves the apparatus toward the eye, probe tip 13, overlain by a central portion of sheath 14, begins to flatten and then to depress the measurement surface, as for example the cornea. This deformation is resisted by the cornea and by the internal pressure of the eye, and shaft 9 begins to move rearward with respect to housing 41, forcing shaft magnet 30 and its accompanying magnetic field toward the opposing stationary magnet 31 as described above generally with respect to FIG. 3. Referring now to FIG. 5.1, as the deformation increases, a depression forms in cornea C at the location P where probe tip 13, covered by a central portion of the sheath 14, presses inward. Concurrently, an edge of the depression forms at regions M of cornea C situated radially away from location P. These regions press rearward against the areas of sheath 14 overlying the edge of annular flange 45, and this rearward pressure causes a rearward displacement of annular tip assembly 40, bushing 11 and magnet 15, with respect to probe tip body 13 and shaft 9. As magnet 15 is displaced rearwardly, the magnetic field of the magnet 15 comes into closer proximity to the sensor 16, which is affixed to shaft 9 by bracket 17. As the magnet 15 approaches the sensor 16, the sensor 16 is exposed to the strengthening field of the magnet 15 and responds by delivering a ratiometric electric current (or potential) in relation to the proximity and strength of the magnet. In other words, the closer the magnet comes to the sensor, the stronger the magnetic field becomes around the magnetic sensor and, consequently, the greater the amount of current which the sensor produces. As the magnet 15 approaches rearwardly toward the magnetic sensor 16, the magnetic field increases as the distance between magnet 15 and magnetic sensor 16 decreases. Because the magnetic sensor 16 is affixed to the shaft 9 via bracket 17, the sensor 16 interprets the strengthening magnetic field as an indication of the positional relationship of the housing 12 to the probe tip 13, indicating the depth of depression of probe tip 13 into the cornea of the eye whose intraocular pressure is being measured.

It will be appreciated that if the apparatus is misaligned as the operator brings it toward the eye surface, that is, if it is not oriented with the front-to-rear axis approximately normal to the eye surface, the eye surface will contact a front part of the probe tip assembly and deform it rearward with respect to the probe tip before the probe tip itself contacts the eye surface. The greater the misalignment, the greater the extent of such early rearward movement of the probe tip assembly, and if the tip position sensor detects a substantial amount (that is, greater than a predetermined threshhold amount) of rearward movement of the probe tip assembly before the shaft position sensor detects any rearward movement of the shaft member, then a misalignment condition is indicated, and the apparatus can automatically so inform the user by a visual or audial signal, or can prevent a measurement being recorded. The operator can then withdraw the apparatus, reapproach the eye surface with improved alignment, and attempt the measurement again. The threshhold can be selected according to the alignment needs presented by the particular measurement being sought.

An alternative arrangement of magnetic field sensing means for determining the relative front-to-rear position of the probe tip assembly is shown in FIGS. 8 and 9. In this example, as in the example described above with reference to FIGS. 4.1 and 5.1, tip magnet 15 is affixed by bracket 17 to bushing 11 in such a position that tip magnet 15 will come into closer proximity to tip position sensor 16 when tip assembly 40 is forced rearward by applying force upon the most forward portion of tip assembly 40, that is, upon at least a portion of the front surface of flange 45. In this example, however, tip position sensor 16 is affixed to the housing 41 rather than to the shaft member 9. In this configuration, as the operator moves the housing toward the eye, deforming the eye surface, the movement of the magnet 15 rearward with respect to the tip position sensor 16 is a sum of the rearward movements of the tip assembly with respect to the shaft member and of the shaft member with respect to the housing. The microprocessor, to which the sensors send their signals, as described more fully below with reference to FIGS. 14 and 15, examines the output of the sensors, and determines the component relative positions by, for example, subtraction of the relative positional data provided by the shaft position sensor 33 from the relative positional data provided by the tip position sensor 15.

In alternative embodiments of the invention, means other than Hall effect sensors can be used either in determining the degree of deformation or in determining the force required to produce the deformation.

ELECTRONIC TREATMENT OF MEASUREMENTS

FIGS. 13 and 14 are block diagrams showing electronic circuitry for use in conjunction with the probe apparatus of the invention. Electrical power supplied by a DC power supply 101, such as a battery, passes to a voltage and amperage 102 regulator to provide a predetermined reference potential and current for the sensitive air pressure transducer bridge and amplifier circuits 104, Hall effect circuits 103 and microprocessor controller circuits 108.

The electronic circuitry includes components that produce pressure data relating to the pressure within the air chamber (in embodiments in which an increase in air chamber pressure caused by deformation of a deformable wall surface of the air chamber by the rearwardly-moving shaft member provides a measure of shaft position), components that are related to the amount of corneal displacement, components that produce signals related to the achievement of preprogrammed test paradigms 108, components related to the display of the test and calibration data 110, 112, components related to the timing of special test situations and components related to the transfer of data to other monitoring devices 111 such as printers, computers, meters and recorders, componenets related to reset circuits 107 for resetting or interrupting the microprocessor 108, and components related to calibration of the Hall effect systems 105, 104 and of the pressure sensor 113.

With reference to FIG. 14, as the cornea and the intraocular pressure force the probe tip assembly and shaft rearward with respect to the housing, pressing the plunger against the deformable wall of the air chamber and increasing the air pressure within the chambers as described above with reference to FIGS. 3 and 4, the pressure transducer produces an electrical analog of the pressure developed within the air chamber. The electrical analog is amplified by a pressure transducer ratiometric amplifier 113 and referenced by a calibration circuit 114 and a signal conditioning circuit, and the resulting potential is sent to an analog to digital (A/D) converter, which can be contained within microprocessor controller 108, which generates a digital representation of the pressure.

The digital pressure signal from the A/D converter can be either directed to another microprocessor for additional treatment, or presented directly to a display driver 110 and then to a display transducer 112, such as liquid crystal display (LCD) which presents the intraocular pressure in terms of millimeters of mercury (mm Hg). Any of various types of audio signal can be produced by the audio signal generator 109, under control of the microprocessor, for informing the operator of the working state of the apparatus, such as, for example, informing that the apparatus is improperly aligned, or a threshhold amount of force has been imposed on the eye surface, or the eye surface has been deformed to a threshhold degree, or a measurement has been made.

Referring now to FIG. 15, for use in embodiments where the rearward force is measured using a Hall effect sensor, pressurer sensor amplifier and calibration circuits 113, 114 are replaced respectively with Hall effect amplifier and calibration circuits 104, 106, which perform generally similar functions.

Because the apparatus according to the invention is capable of simultaneously measuring and recording both the force applied to the eye and the deformation of the eye as a function of the applied force, several different test paradigms exist for achieving a measure of intraocular pressure, for example as follows.

As the device is directed upon the eye, in the manner previously discussed, the microprocessor can be software controlled or programmed to measure the amount of corneal deformation as a function of the force or pressure applied to the eye. In this testing configuration, the device is programmed to measure the deformation of the test site at a predetermined pressure or pressures such as 1, 2, 3, 4, 5, or more mm Hg or any pressures in between these intervals. When a predetermined pressure is reached, the microprocessor automatically measures the amount of deformation of the measurement surface and stores the information for the desired data treatment. Or, alternatively, as the device is directed upon the eye, in the manner previously discussed, the microprocessor may be software controlled or programmed to measure the amount of pressure or force applied as a function of the deformation of the eye when increasing force is applied. In this testing configuration, the device is programmed to measure the pressure on the test site at one or more predetermined deformation amounts. When a predetermined deformation is reached by applying increasing force to the eye, the microprocessor automatically measures or records the amount of pressure required to achieve the appropriate amounts of deformation and stores the information for the desired data treatment.

Or, alternatively, the nearly simultaneous recordings of both pressure and deformation can be sampled at intervals over time by the microprocessor and then stored and treated to achieve a measure of intraocular pressure.

USE

The tonometer apparatus of the invention can be used by an operator with little training and having no special skills, generally as follows.

At the outset the operator fits a sterile sheath over the probe tip assembly, following sterile procedure as will be familiar to health care workers generally. Then the operator presses the reset button 32 and, in embodiments in which the pressure within an air chamber is taken as an analog of the front-to-rear position of the shaft member, pressure equalization port 6 is opened to allow the air pressure within the air chamber and the pressure transducer to equilibrate to atmospheric pressure, which is sampled by the pressure transducer at differential intake port 7. Once equilibration has occurred, pressure equalization port 6 is closed. At this point the pressure within air chamber 2 equals ambient atmospheric pressure, unless or until the atmospheric pressure changes or a force upon probe tip assembly 40 causes shaft 9 to move rearward with respect to housing 1, causing plunger 8 to press against deformable wall 3 of the air chamber.

Once equilibration has been completed, the operator brings the apparatus to the eye, addressing the cornea with the probe tip assembly oriented as nearly normal to the corneal surface as can be estimated. As the operator presses the apparatus forward toward the eye, so that probe tip assembly 40 of the device is gently forced against the corneal surfaces, the resistance exerted by the cornea and by the intraocular pressure causes the shaft member to move rearward against the resistance means.

The probe tip assembly, employing a reawardly-moveable probe tip assembly together with magnetic field position sensing means for determining the extent of deformation of the eye surface according to the invention, can be miniaturized sufficiently that the likelihood of misalignment, and the magnitude of errors resulting from any misalignment that may occur, are substantially reduced.

The operator repeats the attempt if necessary, retreating each time a misalignment signal is heard until the alignment program informs the operator, as described above with reference to FIGS. 14 and 15, that the device has been pressed sufficiently far toward the eye that an depression has been made, to the correct depth. The deformation measuring program will at that moment have instructed the pressure measuring circuitry to hold and display an analog of the intraocular pressure, and the operator can take the pressure measurement from the display.

After the operator has examined the displayed measurement, the circuitry is reset by means of a reset circuit button. The operator can then take additional measurements on the same eye, or can replace the contaminated sheath before making measurements on the next eye. The contaminated sheath is replaced by removing it from the probe tip assembly, and the apparatus is ready to be fitted with a sterile sheath and reequilibrated in preparation for the next measurement.

OTHER EMBODIMENTS

Other embodiments are within the following claims. For example, one or more of the various audible signals can be converted to visual display signals to notify the operator that a measurement has been taken or that the instrument is misaligned.

The probe tip can be pressed into the sclera rather than into the cornea. Because the sclera itself resists deformation more firmly than the corneal wall itself, a specified force against the sclera produces a shallower depression than against the cornea of the same eye. The apparatus can be calibrated to accommodate this difference.

The output of the A/D converter, which can be located within the microprocessor, can be presented to other forms of microprocessors or computers for additional analysis or to save test results in an electronic memory or in a display or printout.

The device can be used without the sheath, but it is preferred that the sheath be used, because it protects the corneal tissues from injury and because it can be discarded between measurements, preventing the spread of disease.

The device can also be used in the practice of tonography by affixing a mass of desired weight (such as, for example, approximately 10 grams) to the probe tip assembly such that it does not come into contact with the eye and does not interfere with the front-to-back movement of the probe tip assembly with respect to the probe tip on the shaft member. With the patient placed in a supine position, the device is directed upon the eye such that only the weight of the floating tip and its coupled 10 gram mass may put pressure upon the measurement area of the cornea. At timed intervals, the operator may apply a downward force upon the instrument, forcing the probe tip against the eye surface and permitting taking a measurement of the intraocular pressure at the point as described above. After having taken the pressure measurement, the information is recorded or saved by the device and the instrument is raised slightly from the eye leaving only the full weight of the tip bearing and its coupled weight to rest upon the eye until the next test interval. This process may be repeated over two, four or more minute intervals, as is customary for tonography.

I claim:

1. Apparatus for measuring pressure within an eye, comprising
    a housing,
    a member interposable between a surface of the eye and a portion of said housing, said member having a rear end and a front end and being substantially non-compressible along its front-to-rear direction, said member being engaged with said housing such that it is frontwardly-and-rearwardly moveable with respect to said portion of said housing,
    means associated with said housing and said member for providing a force resisting rearward movement of said member with respect to said portion of said housing, so that when said member is interposed between the eye surface and said housing portion and said housing portion is moved toward the eye surface, said member front end forms a depression or flattening of the eye surface and said member is moved rearward with respect to said housing against said resisting force, and
    means for determining the position of said member with respect to said portion of said housing.

2. The apparatus of claim 1, further comprising means associated with said member front end for determining the amount of depression or flattening of the eye surface.

3. The apparatus of claim 1 or 2 wherein said means for providing said force resisting rearward movement of said member comprises an elastic membrane having a front surface against which said rear end of said member presses as said member is moved rearwardly with respect to said housing portion.

4. The apparatus of claim 3, said housing portion comprising an air chamber and said elastic membrane comprising a front wall of said air chamber.

5. The apparatus of claim 4 wherein said means for determining said position of said member with respect to said housing portion comprises a pressure sensor responsive to pressure within said air chamber.

6. The apparatus of claim 4 wherein said air chamber comprises a bladder.

7. The apparatus of claim 4 wherein said pressure sensor comprises a pressure transducer.

8. The apparatus of claim 4 wherein said elastic membrane is formed of latex rubber.

9. The apparatus of claim 4, further comprising means for recording said measure.

10. The apparatus of claim 4, further comprising a valve which when open provides communication between said air chamber and atmospheric air.

11. The apparatus of claim 1 or 2, further comprising a prophylactic membrane interposed between said front end of said member and said eye surface.

12. The apparatus of claim 1 wherein said means for determining said position of said member with respect to said housing comprises a Hall effect sensor.

13. The apparatus of claim 1 or 2 wherein said means for providing said force resisting rearward movement of said member comprises a magnet associated with said member and a magnet associated with said housing, the polarities of said member-associated magnet and said housing-associated magnet being oriented such that increasing rearward movement of said member with respect to said housing is increasingly resisted by magnetic repulsion between said magnets.

14. Apparatus for measuring pressure within an eye, comprising
    means for increasingly inwardly deforming a surface of the eye by applying a progressively increasing force onto the surface,
    means for taking a measure related to the amount of the deformation and means for taking a measure related to the amount of said applied force at a sampling time during said progressively increasing force, and
    electronic means responsive to said deformation-related measuring means and said applied force-related measuring means for determining intraocular pressure from the relation between said deformation-related measure and said force-related measure.

15. The apparatus of claim 14, further comprising means for automatically selecting said sampling time.

16. The apparatus of claim 15, said automatically selecting means being capable of selecting a plurality of said sampling times.

17. The apparatus of claim 15, said selected sampling time being a time at which a predetermined force-related measure has been reached.

18. The apparatus of claim 15, said selected sampling time being a time at which a predetermined deformation-related measure has been reached.

19. The apparatus of claim 15, said selected sampling time being the time at the end of a predetermined time interval.

20. The apparatus of claim 14 wherein
said inwardly deforming means comprises a first member having a front end and said progressively increasing force is applied onto said eye surface by directing said front end toward the eye surface and moving said first member toward the eye, and wherein
said means responsive to inward deformation of the eye surface comprises a second member attached to said first member in frontwardly-to-rearwardly moveable relation, said second member being moved increasingly rearwardly with respect to said first member in response to increasing deformation of the eye surface.

21. The apparatus of claim 20 wherein said first member comprises a shaft having a tip that abuts a center of deformation of the eye surface during said inward deformation and said second member comprises a generally cylindrical collar mounted in sliding relation upon said shaft, said collar having a front portion that abuts portions of an annular region of the eye surface radially apart from the center of deformation.

22. A method for measuring intraocular pressure in an eye, comprising
providing means for inwardly deforming a surface of the eye,
contacting said deforming means with a surface of the eye and applying a progressively increasing force to urge said deforming means in a direction toward the eye to increasingly inwardly deform the surface,
measuring the amount of said deformation of the surface and the amount of said applied force at a time during said progressively increasing force, and
determining intraocular pressure from the relation between said measured deformation and said progressively increasing force.

23. The method of claim 22 wherein said time is the time at which a predetermined force is applied.

24. The method of claim 22 wherein said time is the time at which a predetermined deformation has occurred.

25. The method of claim 22, 23 or 24, further comprising measuring the amount of said deformation of the surface and the amount of said applied force at a plurality of times during said increasing force.

* * * * *